(12) United States Patent
Lucas et al.

(10) Patent No.: US 9,072,606 B2
(45) Date of Patent: Jul. 7, 2015

(54) LOCKABLE KNEE IMPLANTS AND RELATED METHODS

(71) Applicants: Clemson University Research Foundation, Clemson, SC (US); University of South Carolina, Columbia, SC (US); Kim John Chillag, Columbia, SC (US)

(72) Inventors: Eric Montgomery Lucas, Clemson, SC (US); John David DesJardins, Clemson, SC (US); Kim John Chillag, Columbia, SC (US); Frank Richard Voss, Columbia, SC (US)

(73) Assignees: Clemson University Research Foundation, Clemson, SC (US); University of South Carolina, Columbia, SC (US)

( * ) Notice: Subject to any disclaimer, the term of this patent is extended or adjusted under 35 U.S.C. 154(b) by 96 days.

(21) Appl. No.: 13/944,161

(22) Filed: Jul. 17, 2013

(65) Prior Publication Data
US 2014/0025174 A1 Jan. 23, 2014

Related U.S. Application Data

(60) Provisional application No. 61/672,352, filed on Jul. 17, 2012.

(51) Int. Cl.
*A61F 2/38* (2006.01)
*A61F 2/30* (2006.01)
(Continued)

(52) U.S. Cl.
CPC . *A61F 2/384* (2013.01); *A61F 2/30* (2013.01); *A61F 2002/30329* (2013.01);
(Continued)

(58) Field of Classification Search
CPC .......... A61F 2/30; A61F 2/38; A61F 2/3836; A61F 2/3886; A61F 2/384; A61F 2/3845; A61F 2/3804; A61F 2/4684; A61F 2/4688; A61F 2/4698; A61F 2/48; A61F 2/2857; A61F 2002/30622; A61F 2002/30474; A61F 2002/30476; A61F 2002/30479; A61F 2002/30481; A61F 2002/30482; A61F 2002/30484; A61F 2002/30492; A61F 2002/30495; A61F 2002/20518; A61F 2002/30522; A61F 2002/30523; A61F 2002/30528; A61F 2002/30662
USPC ..................... 623/18.11–18.12, 20.11–20.13, 623/20.14–20.15, 20.21–20.36, 623/23.39–23.47; 606/55, 60, 62; 27/21.1
See application file for complete search history.

(56) References Cited

U.S. PATENT DOCUMENTS

| | | | |
|---|---|---|---|
| 4,637,382 A * | 1/1987 | Walker | ........................... 606/55 |
| 5,358,527 A | 10/1994 | Forte | |
| 5,800,552 A | 9/1998 | Forte | |
| 6,019,792 A | 2/2000 | Cauthen | |
| 6,217,249 B1 | 4/2001 | Merlo | |

(Continued)

FOREIGN PATENT DOCUMENTS

FR 2868691 10/2005

OTHER PUBLICATIONS

USPTO Non-Final Office Action for related U.S. Appl. No. 13/944,606, mail date Feb. 24, 2015, 18 pages.

*Primary Examiner* — Thomas J Sweet
*Assistant Examiner* — Christie Bahena
(74) *Attorney, Agent, or Firm* — Myers Bigel Sibley & Sajovec, P.A.

(57) ABSTRACT

Total knee replacements for hinged knee implants include a tibial member, a femoral member, a hinge assembly having a laterally extending axle configured to hingedly attach the femoral member to the tibial member, and a lock mechanism in communication with the hinge assembly. The lock mechanism is configured to (i) lock the femoral member in alignment with the tibial member for a full extension or other defined stabile walking configuration to thereby allow an arthrodesis or stiff knee gait and (ii) unlock to allow the femoral and tibial members to pivot relative to each other for flexion or bending when not ambulating.

7 Claims, 10 Drawing Sheets

(51) Int. Cl.
*A61F 2/32* (2006.01)
*A61F 2/48* (2006.01)

(52) U.S. Cl.
CPC .............. *A61F 2/3836* (2013.01); *A61F 2/385* (2013.01); *A61F 2002/3813* (2013.01); *A61F 2/32* (2013.01); *A61F 2/3804* (2013.01); *A61F 2002/30079* (2013.01); *A61F 2002/30492* (2013.01); *A61F 2002/30565* (2013.01); *A61F 2002/30607* (2013.01); *A61F 2002/30622* (2013.01); *A61F 2002/30632* (2013.01); *A61F 2002/30668* (2013.01); *A61F 2002/482* (2013.01)

(56) References Cited

U.S. PATENT DOCUMENTS

| | | | |
|---|---|---|---|
| 7,572,292 | B2 | 8/2009 | Crabtree et al. |
| 7,753,960 | B2 | 7/2010 | Cipolletti et al. |
| 7,799,084 | B2 | 9/2010 | Clemow et al. |
| 8,308,808 | B2 * | 11/2012 | Hershberger .............. 623/20.29 |
| 8,894,714 | B2 * | 11/2014 | Makower et al. .......... 623/20.21 |
| 2003/0208276 | A1 | 11/2003 | Berelsman et al. |
| 2008/0275558 | A1 * | 11/2008 | Clifford et al. ............ 623/20.14 |
| 2009/0171463 | A1 * | 7/2009 | Brehm ....................... 623/20.14 |
| 2010/0131070 | A1 | 5/2010 | Dees et al. |
| 2011/0130835 | A1 | 6/2011 | Ashley et al. |

* cited by examiner

LOCKABLE KNEE IMPLANTS AND RELATED METHODS

RELATED APPLICATIONS

This application claims the benefit of and priority to U.S. Provisional Application Ser. No. 61/672,352, filed Jul. 17, 2012, the contents of which are hereby incorporated by reference as if recited in full herein.

FIELD OF THE INVENTION

The present invention relates to surgical implants and is particularly suitable for knee implants used in the presence of muscular deficiency or as an alternative treatment to knee arthrodesis.

BACKGROUND

Knee arthrodesis, indicated in the presence of inadequate muscular control or soft tissue stability, allows for patients to successfully ambulate. This surgery results in a rigidly extended lower limb that cannot be flexed or reduced in length. The extended position requires greater muscular strength and endurance to control, even when not mobile, which can lead to secondary joint pain and muscular fatigue. The permanence of this rigid extension can also prevent patient participation in many normal daily living activities such as bathing, tying shoes, or sitting in close quarter spaces such as a cars, airplanes and theaters.

Total knee replacement (TKR) is a surgical procedure to relieve pain, correct deformity, and restore knee function using artificial materials to restore the load bearing and movement functions of the knee. If primary treatment fails, a revision procedure is required. As the number of knee replacement procedures increases, so does the incidence of revision surgeries. With each surgery more native anatomy is lost and the risk of secondary damage to musculature, nerves and bone increases. Multiple surgical interventions can compound these risks and negative complications, and can lead to terminal knee dysfunction.

SUMMARY OF EMBODIMENTS OF THE INVENTION

Embodiments of the present invention provide lockable knee implants that allow for knee flexion when desired by the patient, and that lock into a fixed or semi-rigid configuration for structurally stable stance or walking, similar to an arthrodesis or stiff knee gait.

The lockable knee implants can be selectively locked and/or unlocked by a user.

The lockable knee implants can have mechanical or electromechanical locks to lock and unlock the knee implant, and thus the lower limb, into a specific orientation for stance, walking, or the like, or to allow the knee to freely flex for sitting and the like.

The lockable knee implants can include a magnetically operated lock that cooperates with an externally applied magnetic field to lock and unlock the knee implant, allowing the knee to lock the lower limb into a specific orientation for stance, walking or the like, or to allow the knee to freely flex for sitting and the like.

The lockable knee implants can be self-locking, responsive to applying a defined force or load, typically a load-bearing weight.

The lockable knee implants can include buttons, latches or flexible surfaces on the implant that are accessible by the user (through palpation or the like) either manually or with a tool, that can be used to activate the locking or unlocking ability of the implant.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Other systems and/or methods according to embodiments of the invention will be or become apparent to one with skill in the art upon review of the following drawings and detailed description. It is intended that all such additional systems, methods, and/or devices be included within this description, be within the scope of the present invention, and be protected by the accompanying claims.

BRIEF DESCRIPTION OF THE DRAWINGS

Other features of the present invention will be more readily understood from the following detailed description of exemplary embodiments thereof when read in conjunction with the accompanying drawings.

DETAILED DESCRIPTION OF EMBODIMENTS OF THE INVENTION

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. One or more features shown and discussed with respect to one embodiment may be included in another embodiment even if not explicitly described or shown with another embodiment.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "about" means that the recited number or value can vary by +/- 20%.

The term "sterile" means that the noted device or material meets or exceeds defined medical guidelines of cleanliness and is substantially (if not totally) without contaminants so as to be suitable for medical uses.

Figure 1:
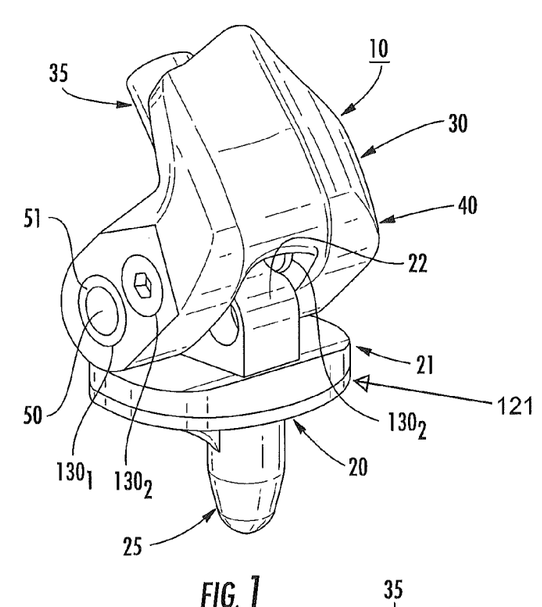
FIG. 1 is an isometric perspective view of a knee implant according to embodiments of the present invention. The device is unlocked and partially flexed.

Turning now to the figures, FIG. 1 illustrates an example of a total knee replacement (TKR) implant 10 according to embodiments of the present invention.

As shown, the implant 10 includes a lower (tibial) member 20, an upper (femoral) member 30 with a locking mechanism 40 (also called a latch). The lower member 20 is attached to the tibia ("T") and the upper member 30 is attached to the femur ("F") via respective stems 25, 35. The lower and upper members 20, 30 can be connected via a hinge yoke 22. The locking mechanism 40 can be incorporated into the hinge that is attached to the rotating platform area 121 using the hinge yoke 22.

Figure 14:
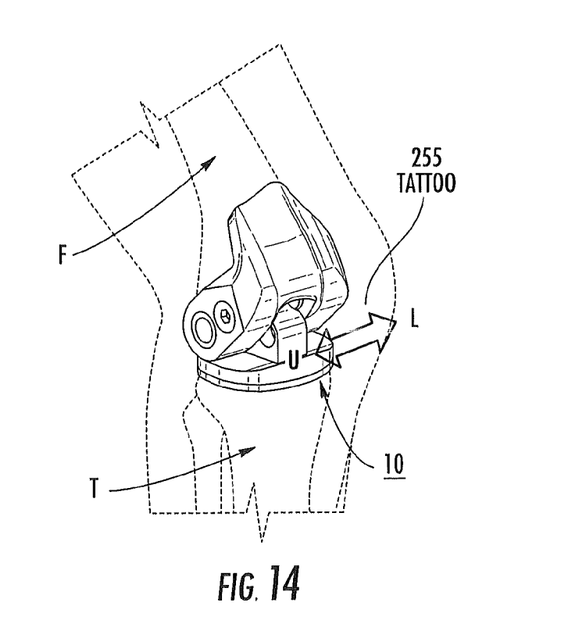
FIG. 14 is an example of a knee implant system in position relative to the femur "F" and tibia "T".

The hinge yoke 22 can include a laterally extending channel or aperture $122_2$ that is aligned with channel $130_1$ in the upper member 30 to hold an axle 50, typically inside an axle bearing 51, so as to allow the upper member 30 to pivot with respect to the lower member 20 via the axle 50. The hinge yoke 22 can include a second channel or laterally extending aperture $122_1$ that holds a moveable locking member 52, shown as a pin or bolt, that can selectively slide to engage or disengage a channel $130_2$ in the upper member 30 to (i) lock into a full stabilization walking configuration (e.g., full extension) to allow an arthrodesis gait without requiring normal muscular strength and/or control and (ii) unlock to allow the members 20, 30 to pivot relative to each other for flexion or bending when not ambulating. FIG. 14 illustrates an exemplary implant 10 in position relative to the femur "F" and the tibia "T".

Figure 7:
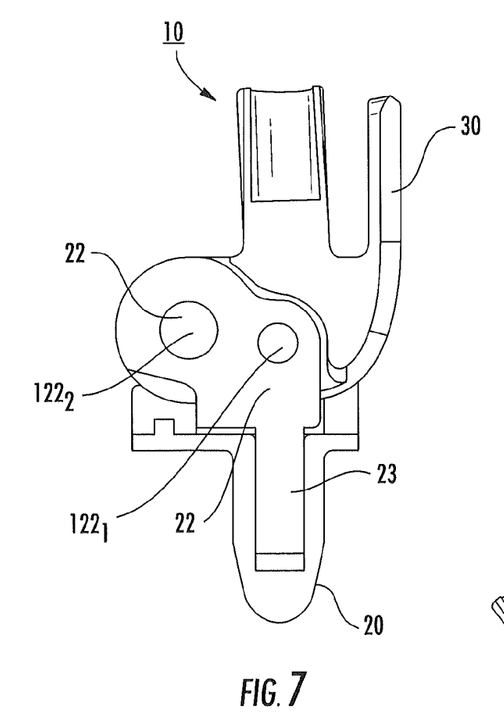
FIG. 7 is a sectioned midplane side view of the device shown in FIG. 1. The device may be locked or unlocked in this position.
Figure 8:
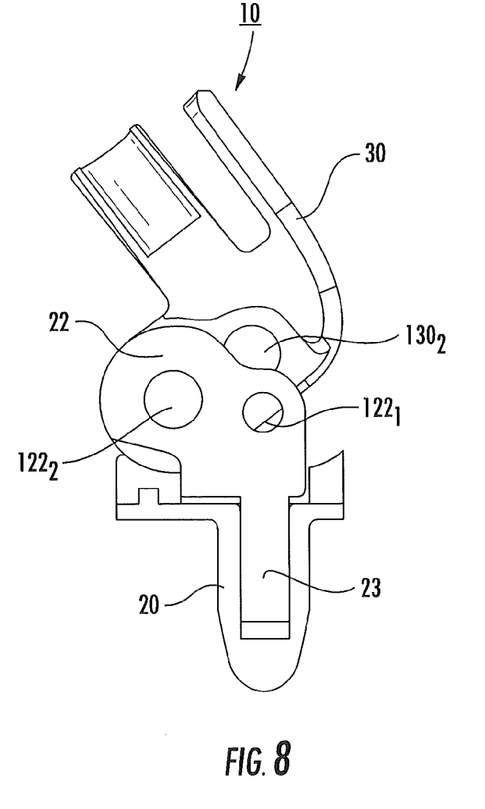
FIG. 8 is a sectioned midplane side view of the device shown in FIG. 1 in a partially flexed orientation. The device is unlocked.

In some embodiments, the hinge yoke 22 can include first and second spaced apart, laterally extending apertures or channels $122_1$, $122_2$ (FIGS. 7, 9), one of which hold the axle 50 as discussed above and the other holding at least one slidable locking member 52. As shown, the axle 50 may be larger than the locking member(s) 52, but the reverse configuration may also be used. The axle 50 can reside behind the locking member(s) 52 as shown. In other embodiments, the axle 50 resides in front of the locking member(s) 52.

In the embodiment shown, at least one slidable locking member 52 includes two locking members, one on each side of the implant 10. The locking members 52 can slide inward and outward substantially in concert, or be separately deployable.

The hinge yoke locking member(s) channel $122_1$ can be configured as a single channel with a constant diameter or with different diameters. Where more than one locking member 52 is used, the different locking members 52 can have different sizes (e.g., diameters) and/or configurations or may have the same configurations and sizes. In the embodiment shown, the hinge yoke 22 includes a forward channel $122_1$ with a reduced diameter or inner extending lip 57 at a medial section thereof 57 (FIGS. 11, 12) or with two aligned laterally extending closed channels (not shown), one for each of the two locking members 52 (where two are used). Although shown as two locking members 52 a single locking member 52 or more than two may be used.

In some embodiments, the implant 10 can include a polymer insert 21 forming part of the hinge/rotating platform as in conventional implants 10. The locking mechanism 40 can be incorporated into conventional or novel hinge/rotating platform systems.

In some embodiments, the insert 21 and/or hinge yoke 22 can be provided in multiple configurations that can be selected by a doctor for a particular patient so that the doctor can choose one that locks the patient's leg 5-10 degrees short of "Full extension" for a stable walking configuration.

The implants 10 can be modular, interfacing with other implantable components of a knee replacement system, allowing for adjustment of limb length and fixation angle. The implants 10 can be suitable for patients who could undergo revision, but are at risk of complications that could compromise its success. The implants 10 can be used for patients with poorly performing revision implants, but who do not desire permanent fusion (or amputation). The implants 10 can be used for patients that otherwise would require fusion or amputation. The implants 10 can be used with patients having existing fusions who can "take-down" to the lockable knee implant to provide them with increased mobility or quality of life. The implants 10 may also be used as a primary implant for a first TKR surgery irrespective of whether a patient may have the compromised tissue or bone structure as a precaution.

The implants 10 can have a hinge/rotating platform design and provide industry standard stability. The locking configurations can be configured to fit modular revision TKRs. The interfacing configurations of modular revision TKR implants can allow mix and match of components to custom fit to individual patients. The implant 10 can restore the knee joint function using a rotating hinge-like function with two axis of articulation, including articulating members 21, 30, which rotate about axle 50, and articulating members 20 and 21, 22 which rotate about the stem 23 (FIG. 7) of the hinge yoke 22, to allow the joint to function in a more normal fashion. In some embodiments, the implant 10 can include a mobile, bearing-type sliding component that supports the yoke 22 and may allow for some Anterior/Posterior (AP) motion (not shown). For descriptions of conventional TKR designs, including rotating, hinged designs, see, e.g., U.S. Pat. No. 5,358,527, 5,800,552, 7,572,292, 7,753,960, 7,799,084, and U.S. PUB 2010/0131070, the contents of which are hereby incorporated by reference as if recited in full herein.

Figures 3, 4:
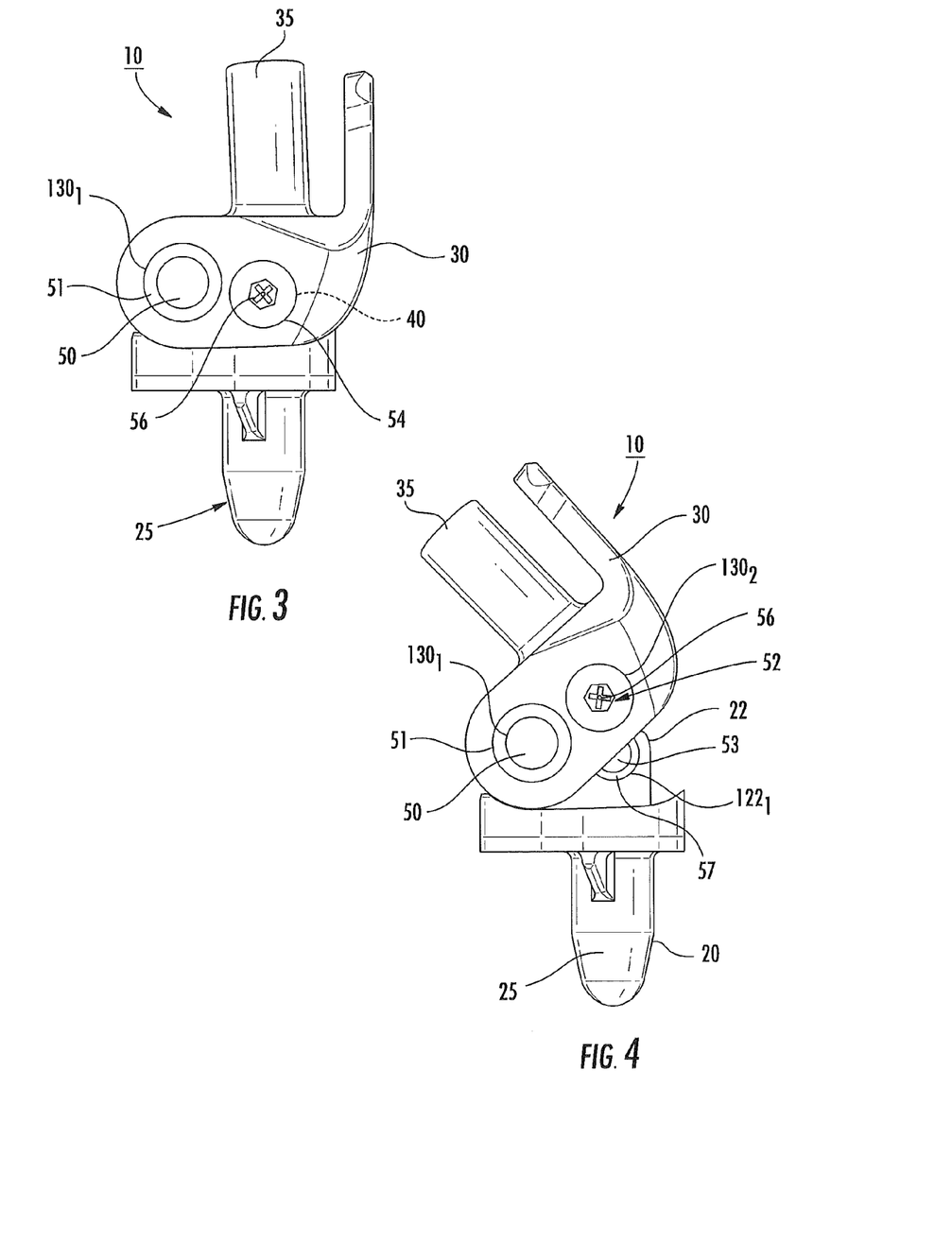
FIG. 3 is a side view of the device shown in FIG. 1. The device may be locked in this position.
FIG. 4 is a side view of the device shown in FIG. 1 in a partially flexed orientation. The device is unlocked.
Figure 5:
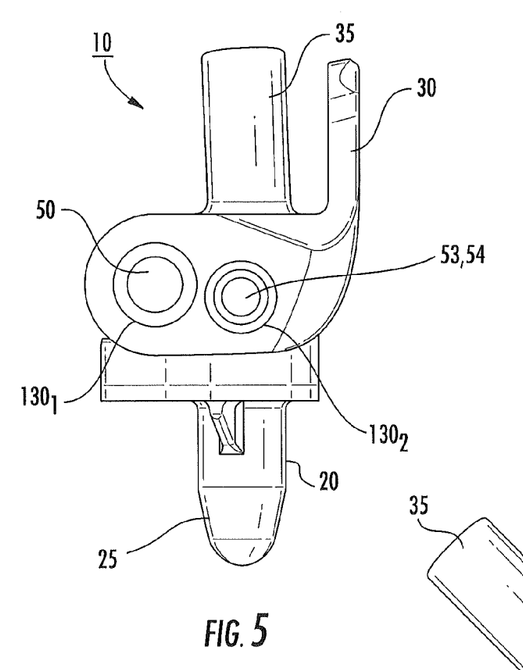
FIG. 5 is a side view of the device shown in FIG. 1 and FIG. 3, with components of the locking mechanism removed.
Figure 6:
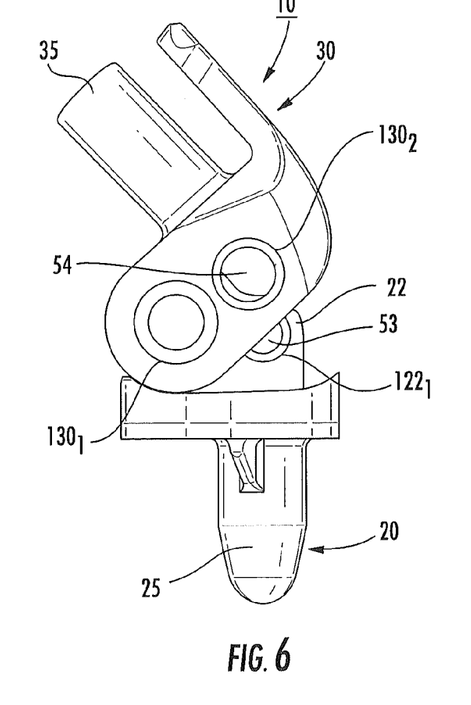
FIG. 6 is a side view of the device shown in FIG. 1 and FIG. 4 in a partially flexed orientation, with components of the locking mechanism removed.

FIGS. 1 and 4 illustrate the implant 10 with the upper member 30 partially pivoted relative to the lower member 20 allowing flexion. FIG. 3 illustrates the implant 10 in a locked upright configuration for stable, weight-bearing walking.

The device 10 can be locked via mechanical or electromechanical locking mechanism 40 that engages the hinge comprising the hinge yoke 22. The locking mechanism 40 is typically unpowered, but may be passively powered (e.g., inductively powered) without requiring an on board power source. The lock can be selectively activated and/or deactivated by a user. The locking mechanism 40 can be manually or electronically activated and/or deactivated.

A user can activate and/or deactivate the locking mechanism from one state to the other. The device 10 can maintain its current status until the user intervenes.

The locking mechanism 40 may be self-activating in response to a large load, such as a load bearing weight, being applied to the members 20, 30, when the members 20, 30 are aligned in a substantially straight or other stable (walking) orientation (such that the pivot shaft of the femoral and tibial components are substantially in-line so that the limb is substantially straight). This activation can be while a patient is prone on a bed or sofa by pushing against a foot board, for example, but is typically in response to standing upright. The activation can be induced by a jolt, small jump or other movement to cause the mechanical lock to move to the lock orientation.

Figure 9:
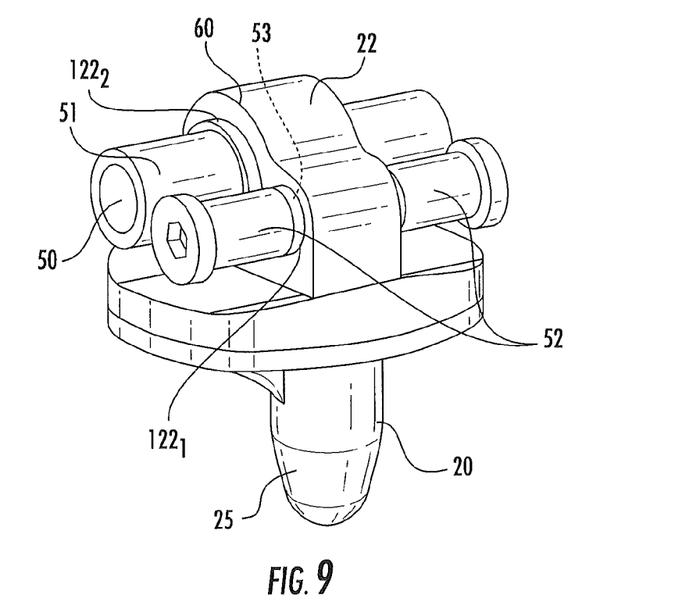
FIG. 9 is an isometric view of the device shown in FIG. 1, and aligned/rotated about its flexion axis as shown in FIG. 3, FIG. 5, and FIG. 7. The device is in an unlocked state, and the femoral component is removed for visibility.
Figure 10:
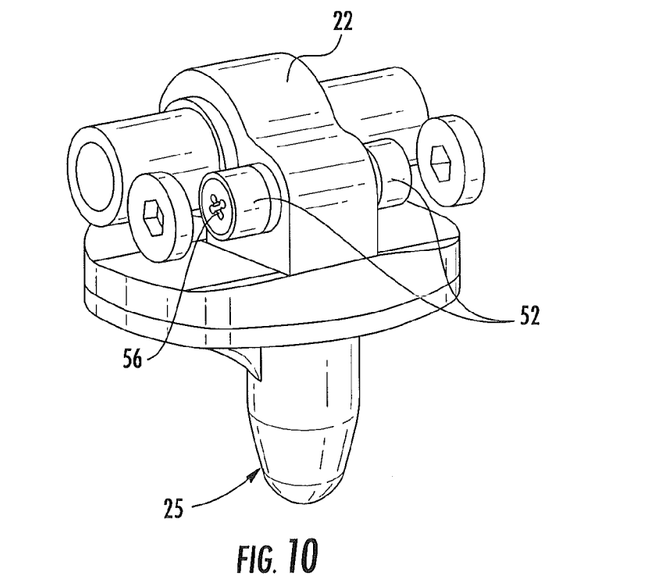
FIG. 10 is an isometric view of the device shown in FIG. 1, and aligned/rotated about its flexion axis as shown in FIG. 3, FIG. 5, FIG. 7, and FIG. 9. The device is in a locked state, and the femoral component is removed for visibility.
Figure 11:
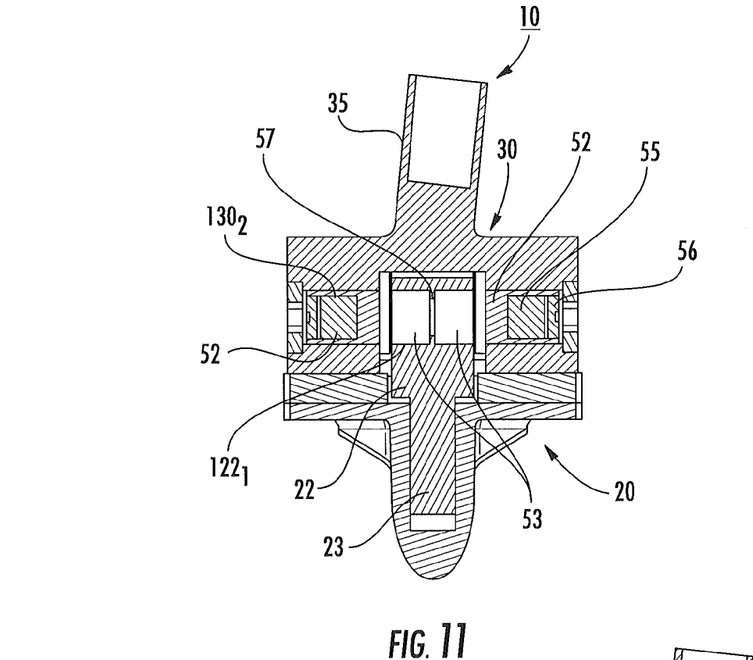
FIG. 11 is a rear view of the device shown in FIG. 1, sectioned in a frontal plane across the center of the locking mechanism. The device is in an unlocked state.
Figure 12:
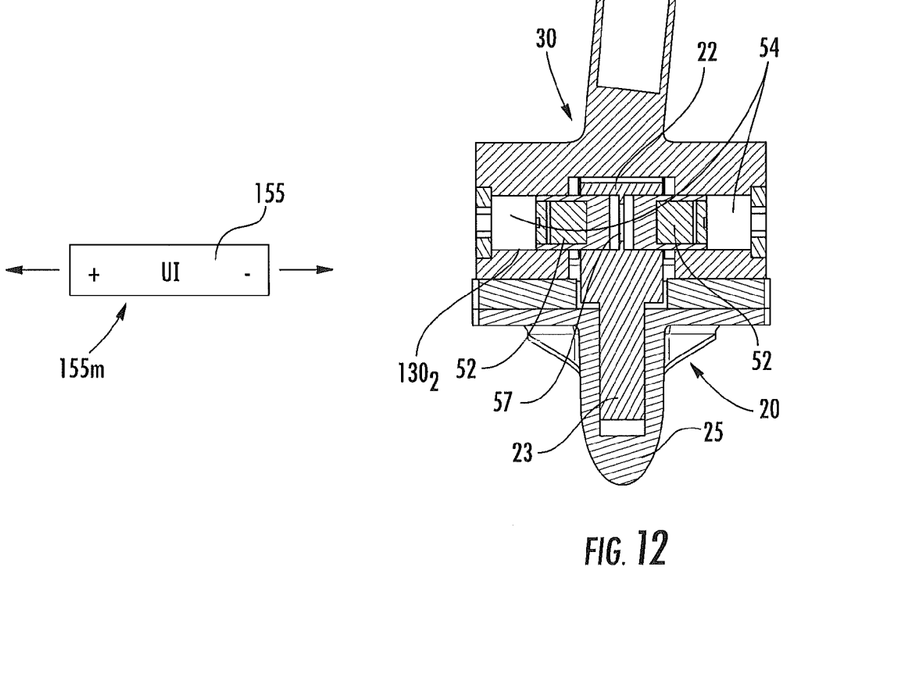
FIG. 12 is a rear view of the device shown in FIG. 1, sectioned in a frontal plane across the center of the locking mechanism, as shown in FIG. 11. The device is in a locked state.
Figure 13:
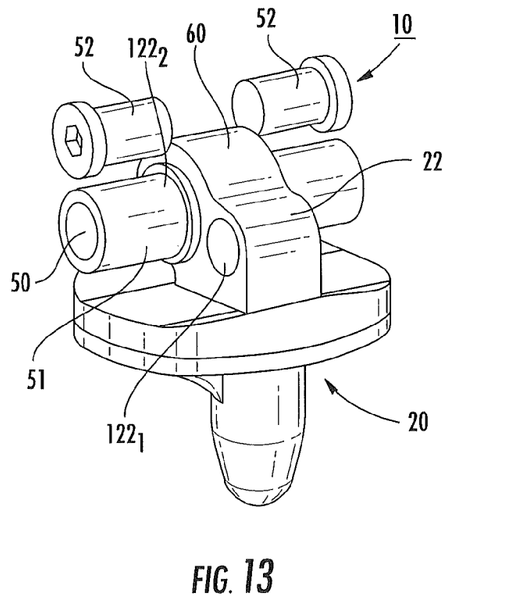
FIG. 13 is an isometric view of the device shown in FIG. 1, and rotated about its flexion axis as shown in FIG. 1, FIG. 2, FIG. 4, FIG. 6, and FIG. 8. The femoral component is removed for visibility. The device is unlocked.

When members 22 and 30 are aligned as shown in FIG. 3, FIG. 5, FIG. 7, FIG. 9, FIG. 10, FIG. 11, and FIG. 12, each locking member 52 can translate axially within interior spaces 53, 54 of channels $122_1$ and $130_2$ to lock and unlock the device 10. The lock is disengaged, as shown in FIGS. 9 and 11, when the locking members 52 reside entirely within the respective internal space 54 of channel $130_2$ of member 30. The lock is engaged, as shown in FIGS. 10 and 12, when one or both locking members 52 are in communication with the interior space 53 of channel $122_1$ of hinge yoke 22, blocking rotation of member 30 with respect to member 22, and thus preventing flexion.

In some particular embodiments, an interruption 57 in the interior channel $122_1$ that divides internal spaces 53 can take the form of a reduced diameter, and can keep locking members 52 from physically contacting either other, or from traveling beyond a pre-determined distance.

When the device 10 is rotated about axle 50, interference geometry 60 of the hinge yoke 22 blocks access of channel $122_1$ and can serve to keep locking members 52 from leaving interior space 54.

Figure 2:
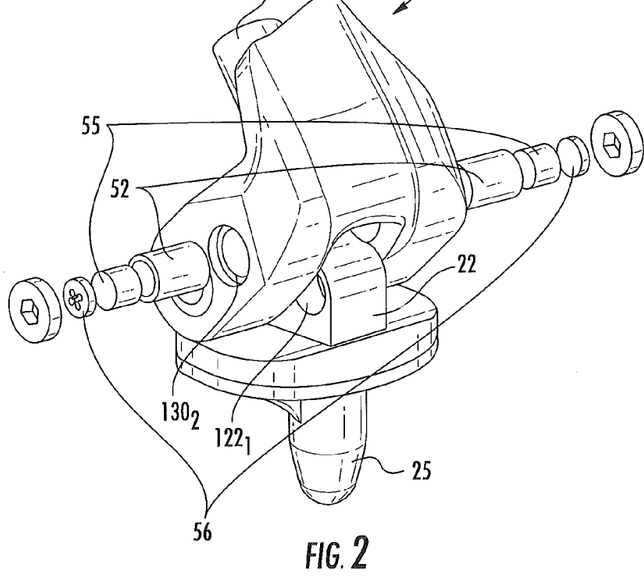
FIG. 2 is an exploded view of the device shown in FIG. 1.

In some embodiments, as shown for example in FIG. 2, the locking mechanism 40 can include a magnetic material 55, which can be a physical "permanent" magnet, that is embedded in, assembled, attached and/or connected to the locking member 52. A cap 56 can be used to seal off the magnetic material 55 from bodily fluid. As shown in FIG. 2, the locking member 52 includes a receiving space that holds the magnetic material 55 therein and cooperates with the cap 56 to seal the magnetic material therein.

With the use of an internal magnetic material 55, attractive or repulsive axial (side-to-side relative to the implant body) force can be applied to the bolts 52 with a user interface device 155 which can apply an external magnetic field (physical or electrical magnet via a user probe, control or other user interface input device), causing the locking member(s) 52 to translate laterally with respect to the implant body 10.

In some embodiments, the polar axis of magnetic material 55 can be in-line with the axis of the lock, and external magnets in the same polar axis can be passed over either side of the device 10, pulling the bolts medially and into an unlocked configuration as shown in FIG. 10 and FIG. 12. By reversing the external magnets to the opposite polar direction, the user can pass the external magnets 155m over either side of the device 10 to move the locking members 52 medially to unlock the device 10 as shown in FIG. 9 and FIG. 11.

FIG. 14 illustrates that a tattoo or other externally visible marker 255 can be applied to the skin of a patient over the locking mechanism 10 to provide alignment information for directional reference for "lock" and "unlock" actions (which can be icons or other suitable visible indicia).

In some particular embodiments, the magnetic material 55 can be a rare earth magnet, which is typically much stronger than ferrous magnets. There are two conventional types of rare earth magnets, neodymium magnets (e.g., neodymium-iron-boron) and samarium-cobalt magnets.

In some embodiments, the polar magnetic axis of magnetic material 55 within locking members 52 can be aligned in such a way that the natural state of the implant is to remain locked until user intervention.

Magnetic material can be extremely brittle and can also be vulnerable to corrosion (such as from the digestive acids in the body). The magnetic material can be sealed within the locking member 52 and cap 56. The magnetic material 55 can be alternatively or additionally plated or coated with a biocompatible material such as polyethylene to protect them from breaking, chipping and/or for corrosion resistance. Particular examples of rare earth magnets include $Nd_2Fe_{14}B$, $SmCo_5$ and $Sm(Co,Fe,Cu,Zr)$.

The magnetic material 55 can include a material that moves or changes viscosity in response to exposure to a magnetic field such as a magnetorheological fluid (also known as an MR fluid, available from Lord Corporation, Erie, Pa.) or a ferrofluid. The fluids change viscosity when subjected to a magnetic field.

Figure 15:
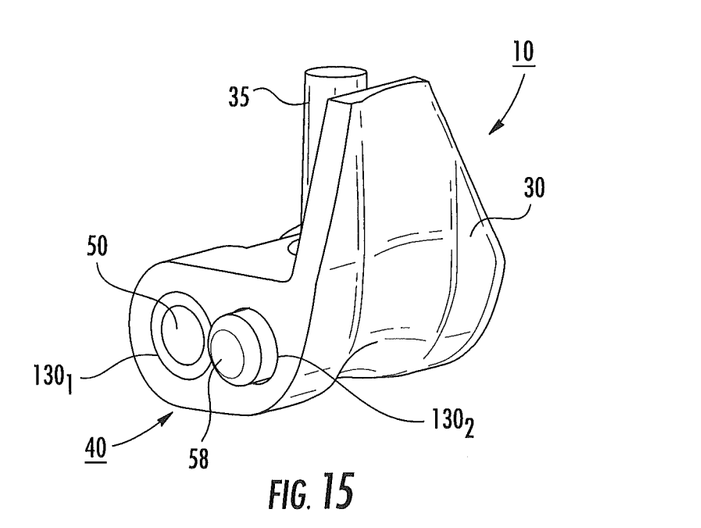
FIG. 15 an example of an embodiment of the device with a mechanical pushbutton for the locking mechanism according to embodiments of the present invention.
Figure 16:
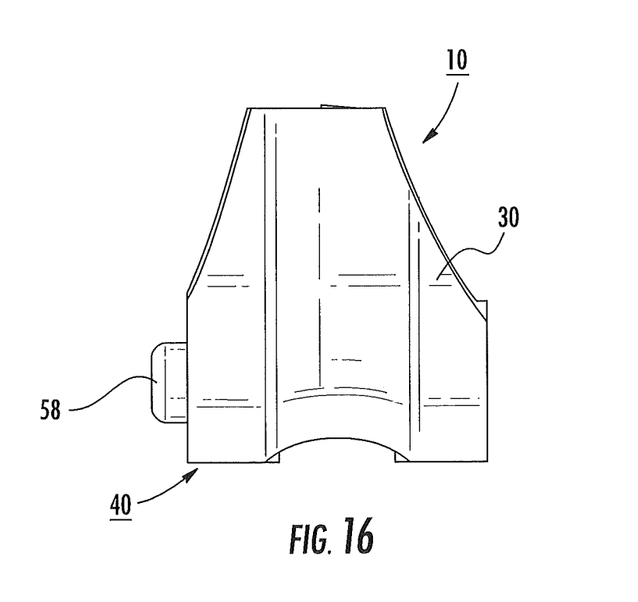
FIG. 16 is front view of the embodiment of the device seen in FIG. 15.

The lock 40 can also or alternatively be a mechanical lock 58, as seen in FIG. 15, that can be manually pushed by a user to engage and/or disengage the locking members 52. For example, a user can push against skin on one side of the implant 10 to slide a pin in a defined direction, e.g., inward or up or down, a distance sufficient to disengage a lock feature that engages or disengages the locking members 52. FIGS. 15 and 16 illustrate an exemplary manually deployable push button 58 that a user can use to engage or disengage the locking mechanism 40, e.g., to slide locking members 52.

In some embodiments, the hinge yoke 22 can include a set of stacked dome or belleview washers, springs or other biasing members that can bias the movement in one direction (to the unlocked or locked position).

The locking mechanism 40 can be self-activating in response to application of load bearing weights as noted above.

The locking mechanism 40 can be a mechanical assembly that includes a set of stacked dome or belleview washers, springs or other biasing members that compress when a defined load is applied and allow a locking member to translate in a defined direction, e.g., sideways or up or down to engage a mechanical lock retention feature associated with the hinge yoke 22.

Figure 17:
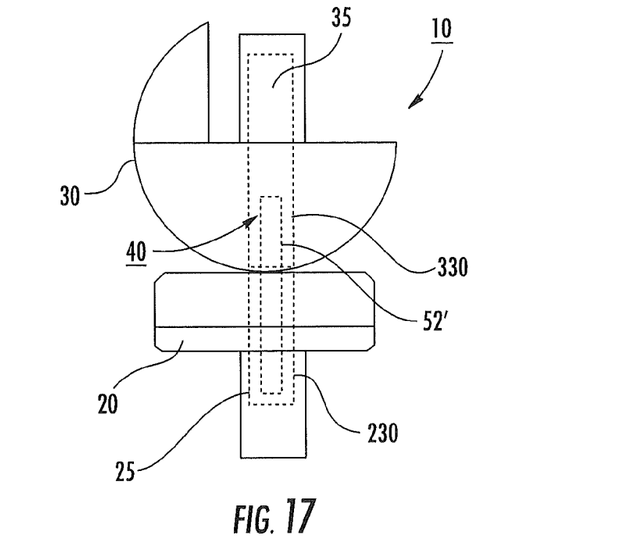
FIG. 17 is an embodiment of the device where the lock can occur vertically through the stem of the femoral and tibial components according to embodiments of the present invention, shown in the locked position.
Figure 18:
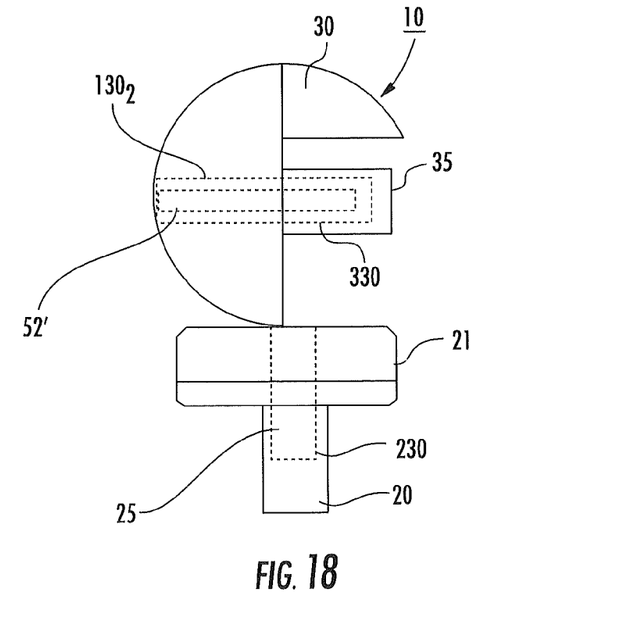
FIG. 18 is a view of the embodiment shown in FIG. 17, in a flexed and unlocked position.

As shown in FIGS. 17 and 18, the locking mechanism 40 can be configured so that locking can occur with a vertical lock member 52', which resides in a channel 330 within the femoral component 30. When the user moves the leg into full extension, locking member 52° can slide down into an aligned channel 230 of tibial component 20. When locking member 52' is in simultaneous communication with both channels 230, 330 flexion cannot occur and the device 10 is thus locked, allowing for ambulation. When the user wishes to unlock the device, the user can lift the leg so that the tibial member is above the femoral member, and the locking member 52' will return entirely to the shaft 330 of femoral member 30, thus unlocking the device and allowing for flexion.

Figure 19:
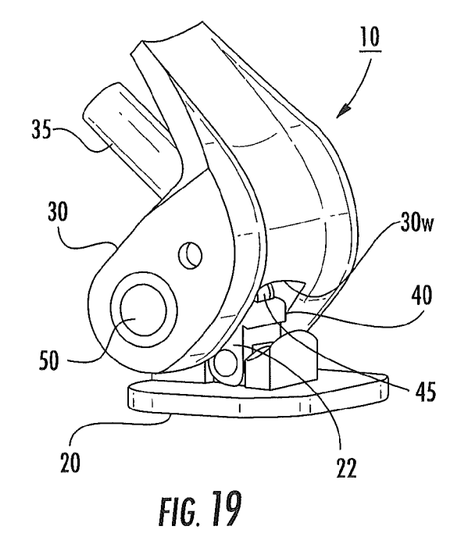
FIG. 19 is an embodiment of the device with another lock mechanism that is configured with a latch that engages when the device moved into full extension and/or a walking stable configuration according to yet other embodiments of the present invention.
Figure 20:
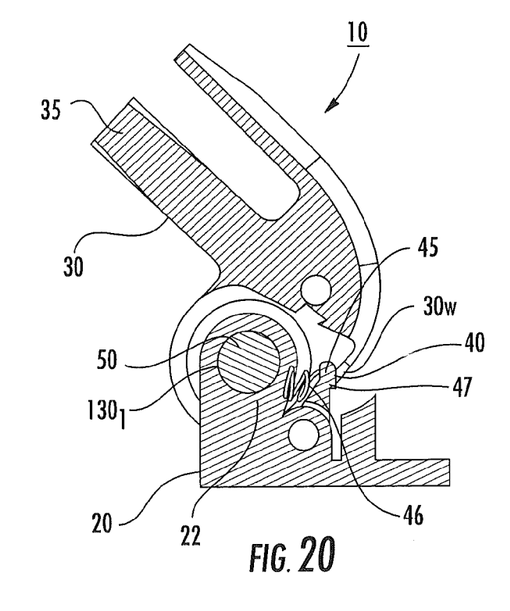
FIG. 20 is a side section view of the embodiment in FIG. 19.

In some embodiments of the device 10, the locking mechanism 40 is configured so that locking can occur in response to when the device is moved into full extension, as shown in FIG. 19 and FIG. 20. The locking mechanism 40 can include an upwardly projecting member 45 that is in communication with a spring or other resilient member 46 to bias the member in one position, e.g., the member 45 can be spring-loaded. The upper femoral component 30 includes an interior wall 30w. The upwardly projecting member 45 has a lip 47 or other shaped feature with a geometry shaped to interface with and secure with a defined depression in the femoral component 30 interior wall 30w. In this embodiment, the locking mechanism 40 can be disengaged through the previously described method of magnetics and/or a mechanical push button.

In other embodiments, the locking mechanism can be activated using an inductively powered circuit/switch based on an externally applied inductive power source.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

That which is claimed:

1. A total knee replacement hinged knee implant, comprising: a tibial member configured to attach to a tibia; a femoral member configured to attach to a femur;

a hinge assembly having a laterally extending axle configured to hingedly attach the tibial member to the femoral member; and a lock mechanism in communication with the hinge assembly configured to (i) lock the femoral member in substantial alignment with the tibial member for a stabilized walking configuration to thereby allow an arthrodesis or stiff knee gait and (ii) unlock to allow the femoral and tibial members to pivot relative to each other for flexion or bending for non-ambulation, wherein the lock mechanism and hinge assembly are internal components that are adapted to reside under the skin of a patient's body, and wherein the lock mechanism is adapted to be selectively actuated by user action external to the patient's body to lock and unlock the implant.

2. The implant of claim 1, wherein the hinge assembly comprises a hinge yoke that has a first channel that holds the axle and at least one spaced apart second channel that holds at least one laterally extending locking member of the lock mechanism that selectively slides in defined directions to respectively lock and unlock the femoral and tibial members.

3. The implant of claim 2, wherein the hinge yoke first channel is a laterally extending channel that holds the axle and the at least one second channel is a laterally extending spaced channel that resides in front of the first channel, wherein the femoral member comprises an axle channel that aligns with the yoke assembly first channel to hold the axle, and wherein the femoral member comprises outer laterally extending locking channels that reside on opposing ends of and align with the at least one second laterally extending second channel, and wherein the at least one locking member can slide, side-to-side, to enter and exit a defined interior space of the at least one second channel of the hinge yoke to lock and unlock the implant.

4. The implant of claim 2, wherein the tibial member has a bearing surface defined by a polymer insert that holds the hinge yoke and allows the femoral member to rotate in a flexion axis relative to the tibial member.

5. The implant of claim 1, wherein the lock mechanism comprises a magnet that slides to lock and/or unlock in response to application of an external magnetic field.

6. The implant of claim 1, wherein the lock mechanism comprises a yoke with a middle open space that receives first and second laterally spaced apart magnets, and wherein the upper member comprises laterally spaced apart lower portions that align with opposing sides of the yoke, the lower portions each having an open interior space, one that receives the first magnet and one that receives the second magnet, and wherein, the magnets slide out of the yoke open interior space into the respective upper member interior space to unlock the lock mechanism and the magnets slide into the yoke interior space to lock the implant in the walking configuration.

7. The implant of claim 1, wherein the lock mechanism comprises at least one magnet or magnetic material that slides in a channel to lock and unlock the implant.

\* \* \* \* \*

UNITED STATES PATENT AND TRADEMARK OFFICE
CERTIFICATE OF CORRECTION

PATENT NO. : 9,072,606 B2
APPLICATION NO. : 13/944161
DATED : July 7, 2015
INVENTOR(S) : Lucas et al.

Page 1 of 1

It is certified that error appears in the above-identified patent and that said Letters Patent is hereby corrected as shown below:

In the Specification:
Column 8, Line 21: Please correct "member 52° can"
to read -- member 52' can --

Signed and Sealed this
Twelfth Day of July, 2016

Michelle K. Lee
*Director of the United States Patent and Trademark Office*